Figure 1:
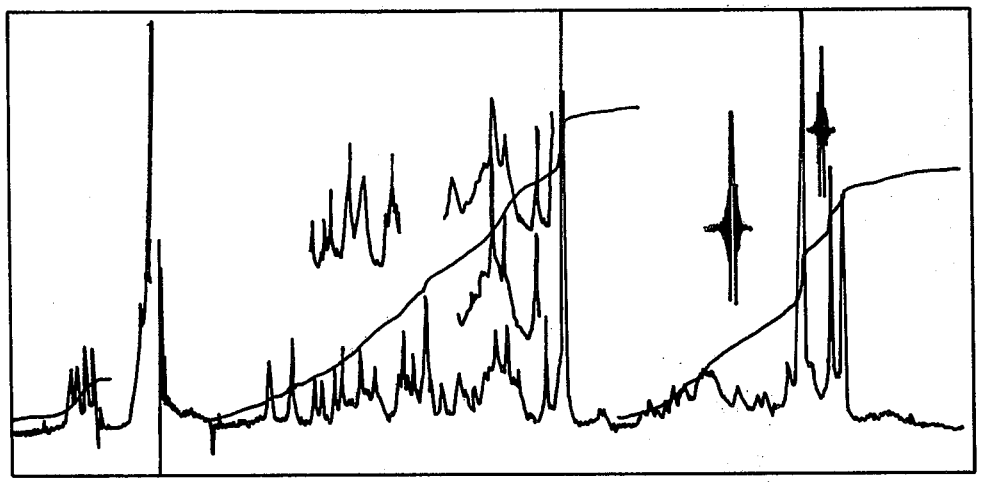

United States Patent [19]

Daniels et al.

[11] 3,984,395

[45] Oct. 5, 1976

[54] METHOD OF ISOLATING GENTAMICIN $C_{2a}$

[75] Inventors: Peter J. L. Daniels, Cedar Grove; Joseph A. Marquez, Montclair, both of N.J.

[73] Assignee: Schering Corporation, Kenilworth, N.J.

[22] Filed: Aug. 19, 1974

[21] Appl. No.: 498,495

Related U.S. Application Data

[63] Continuation-in-part of Ser. No. 269,914, July 7, 1972, abandoned.

[52] U.S. Cl. .............................. 536/17; 195/31 R; 424/181
[51] Int. Cl.² ......................................... C07H 15/22
[58] Field of Search ................. 260/210 AB, 210 R

[56] References Cited

UNITED STATES PATENTS 3,651,042  3/1972  Marquez et al. ............. 260/210 AB Primary Examiner—Johnnie R. Brown
Attorney, Agent, or Firm—Carver C. Joyner; Raymond A. McDonald; Stephen B. Coan

[57] ABSTRACT

Fermentation of *Micromono spora purpurea* NRRL 2953 under controlled aerobic conditions produces a plurality of antibiotic substances including gentamicin $C_{2a}$ which has been heretofore unknown and unrecognized. A method of isolating said antibiotic is described as are the chemical and biological properties of the same.

2 Claims, 2 Drawing Figures

U.S. Patent   Oct. 5, 1976   3,984,395

NUCLEAR MAGNETIC RESONANCE SPECTRUM
OF GENTAMICIN C$_{2a}$

NUCLEAR MAGNETIC RESONANCE SPECTRUM
OF GENTAMICIN C$_2$

METHOD OF ISOLATING GENTAMICIN $C_{2a}$

This application is a continuation in part of copending application Ser. No. 269,914, filed July 7, 1972, now abandoned.

This application relates to a heretofore unrecognized composition of matter produced by *Micromonospora purpurea*. More particularly, the application relates to a novel composition of matter herein designated gentamicin $C_{2a}$ and to a method for isolating it in substantially pure form free from antibiotic substances coproduced therewith.

DESCRIPTION OF THE PRIOR ART

In U.S. Pat. No. 3,091,572 are disclosed a pair of novel *actinomycetes* therein designated, *Micromonospora purpurea* and *Micromonospora echinospora*. Also disclosed are a pair of variant strains of *M. echinospora* namely *M. echinospora* var. *pallida* and *M. echinospora* var. *ferruginea*. All of the disclosed microorganisms share a common property, that of elaborating a novel antibiotic therein designated gentamycin but subsequently named gentamicin. This antibiotic originally believed to be a single entity, when subjected to column chromatography was later found to consist of three closely related substances. The chromatographic technique is described in U.S. Pat. No. 3,651,042 together with the properties of the new substances identified as gentamicin $C_1$, $C_{1a}$, and $C_2$, respectively. Although the solvent system utilized in the prior art process is substantially the same as that used herein, the prior art process is ineffective for the separating the compound of this invention from substances coproduced therewith.

BRIEF DESCRIPTION OF THE INVENTION

We have now found a more refined separation process which permits isolation of a new antibiotic substance, gentamicin $C_{2a}$, which hitherto has been unknown and unrecognized. Thus, the invention sought to be patented, in its composition of matter aspect, is substantially pure gentamicin $C_{2a}$, free from antibiotics co-produced therewith.

The invention sought to be patented in its process aspect relates to a process which comprises separating gentamicin $C_{2a}$ from an antibiotic mixture containing same by (a) dissolving the antibiotic mixture in the upper phase of a solvent system consisting of methanol, chloroform and 17% ammonium hydroxide in the volume ratio of 1:2:1; (b) distributing by counter current means the components of said antibiotic mixture between the upper and lower phase of said solvent system while concurrently moving the upper phase of the solvent system through a counter current extractor; (c) chromatographing to locate the components in said extractor and (d) isolating gentamicin $C_{2a}$ from said solvent system.

THE ANTIBIOTIC

Gentamicin $C_{2a}$ like the other antibiotics produced in the fermentation disclosed in U.S. Pat. No. 3,091,572, is an aminoglycoside antibiotic. It therefore is capable of forming acid addition salts and Schiff base-oxazolidine derivatives which have antibacterial properties.

Gentamicin $C_{2a}$ gives positive results in ninhydrin and Elson-Morgan tests and gives negative results in the maltol, furfural and Sakaguchi tests.

When compared with other known aminoglycoside antibiotics, gentamicin $C_{2a}$ is most similar structurally to gentamicin $C_2$. However, significant differences between the two compounds are extent. For example gentamicin $C_2$ has a specific rotation in water when measured by the D line of sodium at 26° of $+160° \pm 8°$ (C = 0.6%) whereas gentamicin $C_{2a}$ has a specific rotation when measured under substantially the same conditions of $+114° \pm 5°$ (C = 0.3%).

Figure 2:
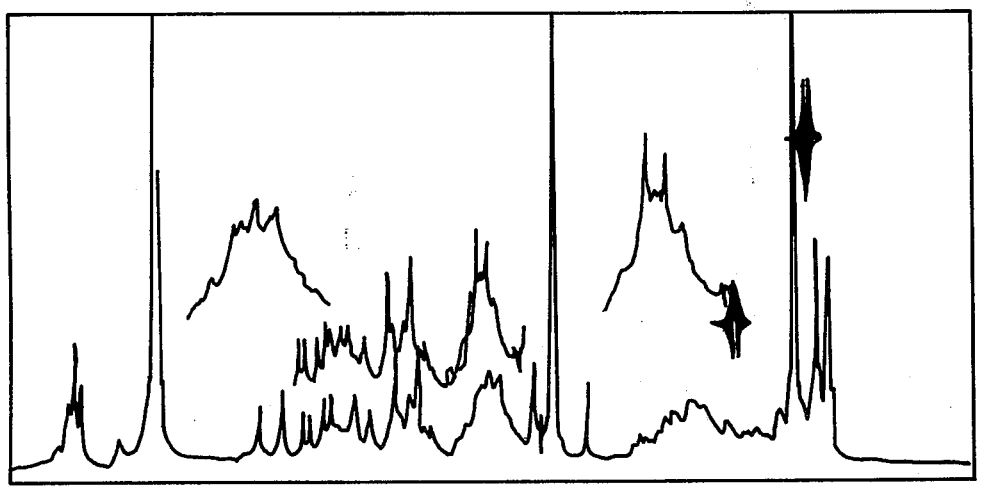

FIGS. 1 and 2 are the nuclear magnetic resonance (NMR) spectra of gentamicin $C_{2a}$ and gentamicin $C_2$, respectively.

The spectra result from a scan of a solution of the respective antibiotics in deuterium oxide ($D_2O$) with no internal reference. The HDO peak is placed at delta $(\delta) = 4.7$ (PPM), thus the spectral scans are about 0.5 – 5.5 parts per million (PPM) from tetra-methylsilane (TMS). The two spectra differ significantly in the coupling constants for protons about the respective C-6' asymmetric carbon atoms. For gentamicin $C_2$ the coupling constant between the protons attached to carbons 5' and 6' $J(H_5, H_6)$ is $5.3 \pm 0.2$ Herz (Hz); for gentamicin $C_{2a}$ the constant is $6.5 \pm 0.2$ Hz. In view of the similarity of other spectral parameters, this difference is consistent with a gentamicin $C_{2a}$ structure which differs from the gentamicin $C_2$ structure in the stereochemistry about carbon 6'.

Stepwise degradation of the two antibiotics to their respective 2,6-diaminosugar units, isolated as their di-N-acetyl methyl glycoside derivatives, followed by spectral and optical rotation measurements of the derivatives reveals that the gentamicin $C_2$ derivative has the R configuration at C-6' and may, therefore, be represented by the formula shown in FIG. 1, whereas the corresponding gentamicin $C_{2a}$ derivative has the S configuration at C-6' and may therefore be represented by the formula shown in FIG. 2 (Haworth projection).

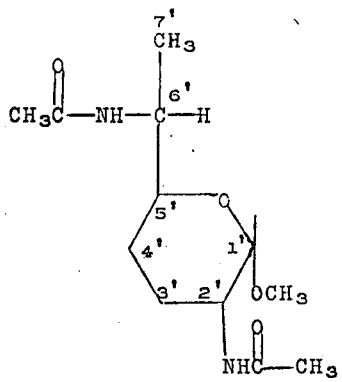

1

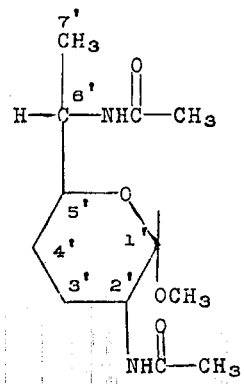

2

| From gentamicin $C_2$ | From gentamicin $C_{2a}$ |
|---|---|
| A crystalline solid M.P. 261°–262° $\alpha_D^{25} = +195°\pm10°$ C = 0.39% $CH_3OH$ | An amorphous solid having no discrete melting point $\alpha_D^{25} = +29°\pm4°$ C = 0.09% $CH_3OH$ |

Additionally, gentamicin $C_{2a}$ has a molecular weight of 463 as determined by mass spectrometry which is consistent with an empirical formula of $C_{20}H_{41}N_5O_7$.

On the basis of the foregoing, gentamicin $C_{2a}$ may be depicted as set forth in Formula 3 below having the stereochemistry shown.

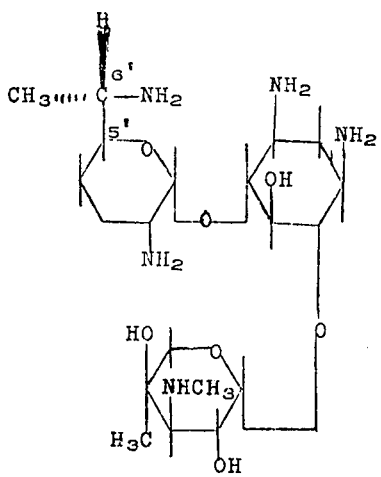

BIOLOGICAL ACTIVITY

Gentamicin $C_{2a}$ exhibits substantially the same antibacterial spectrum in vitro as do gentamicin $C_1$, $C_{1a}$, and $C_2$. Thus, the antiobiotic may be used for substantially the same anti-bacterial indications and in the same manner as disclosed in U.S. Pat. No. 3,091,572. For example, it is useful in wash solutions, for sanitary purposes, as in the washing of hands and the cleaning of equipment in contaminated rooms.

In Table 1, set forth below is shown the in vitro minimal inhibitory concentration (MIC) of gentamicin $C_{2a}$ against representative gram-positive and gram-negative bacteria. The results are derived using the standard tube dilution method in Mueller-Hinton broth.

Table 1

| Organism | MIC | (mcg/ml) |
|---|---|---|
| *Escherichia coli* | ATCC 10536 | 0.3 |
| | La290R55 | 17.5 |
| | JR66 | 7.5 |
| *Pseudomonas aeruginosa* | 762 | 0.8 |
| | 3223 | 0.3 |
| | 20 | 3.0 |
| | St 138 | >25* |
| | Travers | >25* |
| *Klebsiella pneumoniae* | 17 | 0.8 |
| | 3694 | 17.5 |
| *Salmonella typhi. B.* | | 0.3 |
| *Staphylococcus aureus* | 6538P | 0.3 |
| | Ziegler | 0.3 |
| | 59N | 0.3 |
| *Streptococcus pyogenes* | C | 7.5 |
| *Bacillus subtilis* | 663 | 0.1 |

*Gentamicin resistant.

The acute intravenous $LD_{50}$ of gentamicin $C_{2a}$ is 110 mg/kg when determined in male CF-1 (Carworth Farms) mice weighing 20 grams each. The acute intraveneous $LD_{50}$ of gentamicin $C_2$ under the same test conditions is 83 mg/kg.

EXAMPLE 1

Separation of Gentamicin $C_{2a}$ From Co-produced Antibiotics

Dissolve 96 gms. of gentamicin base (prepared as described in Example 4 of U.S. Pat. No. 3,091,572) in 400 ml. of the upper phase which results when methanol, chloroform and 17% ammonium hydroxide are mixed in the volume ratio of 1:2:1. Add one tenth of the solution to each of the first 10 tubes in a 500 × 80 ml. tube counter current extractor. Fill all of the tubes including the first 10 to capacity with the lower phase of the above-described solvent mixture. Set the solvent reservoir to deliver 40 ml. of upper phase to tube one for each transfer. Set the apparatus for 500 transfers. When the transfers are complete, sample every eighth tube for chromatography (in duplicate) on Schleicher and Schuell paper No. 589 using the lower phase of the above-described solvent mixture. Permit the chromatograms to develop for about 16 hours then dry the papers. Plate one paper on an agar plate seeded with *Staphylococcus aureus* (A.T.C.C. 6538P), spray the duplicate with the conventional ninhydrin solution and heat to develop. Incubate the agar plate at 37°C overnight and combine the solution from tubes containing the material that migrates like gentamicin $C_1$ (i.e. tubes 290–360).

Replace tubes 290–360 with fresh tubes containing 40 ml. of upper phase and 40 ml. lower phase. Re-set the apparatus for an additional 2800 transfers and repeat the chromatographic procedure performed above. Combine tubes 1–16 and concentrate in vacuo to obtain 1.3 gms. of Antibiotic $C_{2a}$.

EXAMPLE 2

Dissolve 904 mg. of gentamicin $C_{2a}$ in 100 ml. of water and using 6N $H_2SO_4$ adjust to pH 4.5. Stir the solution with Darco G60 for about ½ hour, and filter. Concentrate the filtrate and add to an excess of methanol. The resulting precipitate is filtered and dried to yield 470 mgs. of gentamicin $C_{2a}$ sulfate.

Alternatively, by substituting an equivalent amount of mineral acid such as, hydrochloric acid, phosphoric acid, hydrobromic acid, or the like and following substantially the process of Example 2 the corresponding acid addition salts may be prepared.

EXAMPLE 3

Dissolve 356 mg. of gentamicin $C_{2a}$ sulfate salt as prepared in Example 2 in 12 ml. of deionized water and pass through a column 2 cm × 25 cm (O.D. × height) of IRA 401S resin ($\overline{OH}$ cycle). Elute the column with deionized water. Concentrate the eluate and lyophilize to obtain 155 mg. of gentamicin $C_{2a}$ assaying 742 mcg/mg which moves as one spot and migrates 23 ± 1 cm in 16 hours upon being chromatographed by the method described in Example 1.

We claim:

1. A process which comprises separating gentamicin $C_{2a}$ from an antibiotic mixture containing same by (a) dissolving the antibiotic mixture in the upper phase of a solvent system consisting of methanol, chloroform and 17% ammonium hydroxide in the volume ratio of 1:2:1; (b) distributing by counter current means the components of said antibiotic mixture between the upper and lower phase of said solvent system while concurrently moving the upper phase of the solvent system through a counter current extractor; (c) chromatographing to locate the components in said extractor and (d) isolating gentamicin $C_{2a}$ from said solvent system.

2. A process of claim 1 wherein the separation consists of two distributing steps.

* * * * *